United States Patent [19]

Rauh

[11] Patent Number: 4,892,834

[45] Date of Patent: Jan. 9, 1990

[54] CHEMICAL SENSOR

[75] Inventor: R. David Rauh, Newton, Mass.

[73] Assignee: EIC Laboratories, Inc., Norwood, Mass.

[21] Appl. No.: 92,458

[22] Filed: Sep. 3, 1987

Related U.S. Application Data

[63] Continuation-in-part of Ser. No. 894,285, Aug. 7, 1986, abandoned.

[51] Int. Cl.[4] ............................................. G01N 27/00
[52] U.S. Cl. .................................... 436/149; 73/23; 324/71.6; 422/58; 422/88; 422/98; 436/113; 436/144
[58] Field of Search ............................. 422/98, 58, 88; 436/144, 113, 149; 73/23; 324/71.5

[56] References Cited

U.S. PATENT DOCUMENTS

| | | | |
|---|---|---|---|
| 3,479,257 | 11/1969 | Shaver | 436/144 |
| 3,831,432 | 8/1974 | Cox | 73/23 |
| 4,045,729 | 8/1977 | Loh | 422/98 X |
| 4,197,089 | 4/1980 | Willis | 422/98 X |
| 4,324,760 | 4/1982 | Harris | 422/98 |
| 4,324,761 | 4/1982 | Harris | 422/98 |
| 4,423,407 | 12/1983 | Zuckerman | 422/98 X |
| 4,542,640 | 9/1985 | Clifford | 73/23 |

OTHER PUBLICATIONS

Harris, J. Electrochem. Soc.: Solid-State Science and Technology, 2657–2662 (1980).
Shaver, Appl. Phys. Lett., 11: 255 (1967).
Yamamoto et al., Surface Science, 92: 400 (1979).
Poteat et al., J. Elec. Mat., 12: 18 (1983).
Steele et al., Appl. Phys. Lett., 28: 687 (1976).
Yamamoto et al., J. Appl. Phys., 52: 6227 (1981).
Nylander et al., J. Appl. Phys., 56: 1177 (1984).
Armgrath et al., J. Appl. Phys., 56: 2956 (1984).
Abe et al., IEEE Transactions of Electron Devices, 26: 1939 (1979).
Maclay et al., IEEE Transactions on Electron Devices, 32: 1158 (1985).
Dobos et al., IEEE Transactions on Electron Devices, 32: 1165 (1985).
Zemel et al., Anal. Chem., 47: 255A (1975).
Windischmann et al., J. Electrochem. Soc.: Solid-State Science and Technology, pp. 627–633 (1979).
Heyne et al., J. Electrochem. Soc.: Solid-State Science and Technology, pp. 727–735 (1977).
Nelson et al., (Source Unknown).
Seiyama et al., (Source Unknown) (1962).
Clifford et al., Ind. Res. and Dev., pp. 143–147 (1982).
Zemel, Research/Development, pp. 38–44 (1977).
Saaman et al., Sensors and Actuators, 7: 75 (1985).
Lundstrom et al., "Gas-Sensitive Metal Gate Semiconductor Devices," in *Solid State Chemical Sensors*, pp. 1–63, (1985).
Raun et al., Appl. Phys. Lett., 45: 352 (1986).

Primary Examiner—Barry S. Richman
Assistant Examiner—Jill Johnston
Attorney, Agent, or Firm—Fish & Richardson

[57] ABSTRACT

A sensor for detecting a chemical substance includes an insertion element having a structure which enables insertion of the chemical substance with a resulting change in the bulk electrical characteristics of the insertion element under conditions sufficient to permit effective insertion; the change in the bulk electrical characteristics of the insertion element is detected as an indication of the presence of the chemical substance.

25 Claims, 3 Drawing Sheets

CHEMICAL SENSOR

BACKGROUND OF THE INVENTION

The United States Government has rights in this invention pursuant to contract No. N00014-84-C-0758 awarded by The Department of the Navy, and NASA Contract NAS7-986.

This application is a continuation in-part of Rauh, U.S. Ser. No. 894,285, filed Aug. 7, 1986, now abandoned.

This invention relates to detecting chemical substances.

Solid state chemical sensors are semiconductor based devices which can detect chemical substances, e.g., hydrogen. One type of solid state sensor is the Schottky barrier diode sensor. Harris, J. Electrochem. Soc.: Solid-State Science and Technology, 2657-62 (1980), describes a Schottky barrier diode sensor for detecting hydrogen in which a polycrystalline $TiO_2$ semiconducting film is disposed between a Pt film and a Ti film. A Schottky barrier exists at the $Pt/TiO_2$ interface and forms the basis of the sensor's ability to detect hydrogen. Upon exposure to hydrogen, hydrogen atoms diffuse into the $TiO_2$ film and ionize, causing the barrier height, and thus the resistance, of the diode to decrease. The decrease in resistance can be measured as an indication of hydrogen concentration.

Another type of solid state chemical sensor is based on metal-insulator-semiconductor (MIS) or metal oxide semiconductor (MOS) capacitors. In these sensors, a catalytic film (i.e., one which dissociates molecules) is separated from a semiconductor film by a dielectric film. Exposure to a gas, e.g., hydrogen, changes the capacitance of the sensor. The change in capacitance can be measured as an indication of gas concentration.

Chemical sensors not based on semiconductors are also known. Shaver, Appl. Phys. Lett., 11:255 (1967), describes a hydrogen sensor employing a $WO_3$ film contacted at two edges by metal electrodes. A "small amount" of Pt is disposed on the surface of the $WO_3$ film to "activate" the $WO_3$. Exposure to hydrogen at elevated temperatures (250–400° C.) causes the surface resistivity of the $WO_3$ film, measured across the film, to decrease; the magnitude of the decrease is related to hydrogen concentration.

SUMMARY OF THE INVENTION

In general, the invention features a sensor that includes an insertion element having a structure which enables insertion of a chemical substance with a resulting change in the bulk electrical characteristics of the insertion element; and detecting means for detecting the change in the bulk electrical characteristics of the insertion element as an indication of the presence of the chemical substance. (As used herein, the term "bulk electrical characteristics" refers to the electrical characteristics, e.g., conductivity, dielectric constant, etc., throughout the thickness of the insertion element. In contrast, the term "surface electrical characteristics" refers to the conductivity confined to the surface, e.g., the first few atomic layers, of the insertion element.) In one aspect, the detecting means measures the change in capacitance of the sensor as a manifestation of the change in bulk electrical properties of the insertion element.

The detecting means can also include first and second electrically conductive elements that sandwich the insertion element. The first electrically conductive element preferably includes a catalytic element, preferably Pt, Pd, Cu, Ru, Ni, or Au, which serves to dissociate the chemical substance into species that can insert into the bulk of the insertion element, and the second electrically conductive element preferably includes a metal, e.g., aluminum; a semiconductor, e.g., p type or n type Si; or an electrically conductive ceramic, e.g., indium tin oxide (ITO). Suitable materials for the insertion element include $WO_3$, $IrO_2$, and $HfS_2$. Preferably, the sensor further includes a dielectric element, e.g., $SiO_2$ or $Ta_2O_5$, in electrical contact with the insertion element, and the dielectric element and insertion element are sandwiched between first and second electrically conductive elements described above. The chemical substance preferably includes hydrogen or ammonia. Examples of hydrogen-containing chemical substances that can be sensed include hydrogen gas, ethanol, and ammonia. Where the second electrically conductive element includes a semiconductor, the sensor is preferably incorporated as part of a field effect transistor.

The invention also features a method for detecting a chemical substance, including the steps of providing a sensor including an insertion element; contacting the sensor with the chemical substance under conditions sufficient to permit effective insertion, whereupon the chemical substance inserts into the bulk of the insertion element and causes the bulk electrical characteristics of the insertion element to change; and detecting the chemical substance based on the change in the bulk electrical characteristics of the insertion layer. Preferably, the sensor is operated at temperatures less than 150° C., and, more preferably, at room temperature.

The invention provides chemical sensors which can be used to detect any chemical substance that can insert into the insertion element of the sensors or of dissociating, e.g., in the presence of a catalyst, to form insertable species. The sensors exhibit rapid detection and clearing responses because the inserted materials are highly mobile within the insertion element. Moreover, the sensors can be used over a wide range of chemical concentrations because they are sensitive at low concentrations but do not saturate readily, even at high concentrations, as a result of the many insertion sites that exist. The selectivity of the sensors can be modulated by adjusting the lattice constant of the insertion element.

The sensors can be used over a broad temperature range, including room temperature. The ability of the sensors to operate at relatively low temperatures (i.e. compared to conventional sensors which typically operate above 250° C.) makes them useful in silicon-based integrated circuits, which cannot be operated effectively above about 150° C. Furthermore, the use of external heaters can be avoided.

Other features and advantages of the invention will be apparent from the following description of the preferred embodiments thereof, and from the claims.

DESCRIPTION OF THE PREFERRED EMBODIMENTS

We first briefly describe the drawings.

STRUCTURE

Figure 1:
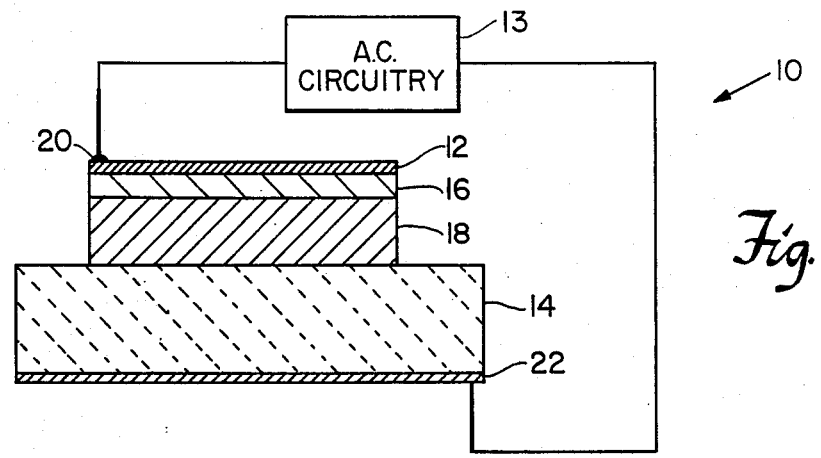
FIGS. 1 and 2 are fragmentary diagrammatic cross-sectional views, respectively, of a sensor embodying the invention, and a field effect transistor incorporating a sensor embodying the invention.

A chemical sensor 10 employing an insertion element 16 is shown in FIG. 1. Insertion element 16 is a film having an open lattice structure which permits insertion of atoms or molecules. Insertion occurs through two mechanisms, depending upon the species being inserted. The first mechanism is electron transfer. According to this mechanism, the atoms or molecules (inserted species) insert into the bulk of element 16 and ionize to form electrons and charge-compensating ions, thereby increasing the bulk electrical conductivity of element 16; the conductivity is proportional to the concentration of inserted species. The increase in the bulk conductivity of element 16 forms the basis of the ability of sensor 10 to detect chemical substances, e.g., hydrogen, which ionize in the described manner. Both the electrons and ions are highly mobile throughout the bulk of element 16. Thus, element 16 exhibits both electronic and ionic conductivity.

The second mechanism is physisorption. According to this mechanism, the atoms or molecules physically adsorb onto the surface of insertion element 16 and then diffuse through its bulk structure without ionizing. The insertion process changes the dielectric constant of element 16, which in turn can be detected as an indication of the inserted species.

To enable sensor 10 to operate at reduced temperatures (i.e. $<150°$ C.), it is necessary that the initial insertion process be energetically favorable (i.e. the change in free energy associated with it must be negative). This provides a thermodynamic driving force for the insertion. Furthermore, the inserted species must be highly mobile throughout element 16 because the response rate of sensor 10 is related to the diffusion rate of the inserted species through element 16.

High mobility requires that there be a proper size match between the inserted species and the channels or voids in the microstructure of element 16 through which these species diffuse. For example, $HfS_2$, a crystalline layered chalcogenide compound, is suitable for detecting ammonia because the Van der Waals spacing between the layers is large enough to accommodate the ammonia molecule. In the case of oxides such as $IrO_2$ and $WO_3$, which are the preferred materials for hydrogen detection, it is desirable to use amorphous materials because the lower densities (30-75% reduction compared to single crystal) give rise to more space-filling voids for accommodating the inserted hydrogen atoms. This in turn leads to higher mobilities throughout insertion element 16.

The thickness of element 16 preferably ranges from 1000 to 10,000 A. Suitable materials for element 16 include single crystalline, polycrystalline, and amorphous insertion compounds. Examples of suitable materials include trioxides, e.g., $WO_3$, $MoO_3$, and $ReO_3$; dioxides, e.g., $WO_2$, $MoO_2$, $ReO_2$, $OsO_2$, $RuO_2$, $PbO_2$, $PtO_2$, $TiO_2$ (amorphous) and $IrO_2$; $M_xO_y$, where $y/x=2-3$ and M is V, Cr, W, Mo, Ta, or Re; M where $y/x=1-2$ and M is Co, Fe, Rh, or Ni; $M_xO_y$, where $y/x=0.5-1$ and M is Cu; solid solutions of $MO_2+TiO_2$, where M is Ir, Re, or Os; PdO; layered chalcogenides having the formula $MX_2$, where M is W, Mo, Zr, Hf, Ta, Ti, Ni, or V, and X, independently, is S, Se, or Te; GaX or $NiPX_3$, where X is S, Se, or Te; $SnS_2$; $\beta$-$ZrNX$, where X is Cl or Br; cubic bronzes having the formula $M_x(QO)_{3+(x/2)}$, where $x=0.05-0.3$, M is K, Cu, Ag, or Cs, and Q, independently, is W or Mo; and $M_xVO_{y+x/2}$, where $y=1-2$, $x=0.05-0.3$, and M is K, Cu, Ag, or Cs. These materials can also be alloyed with one another. The particular material chosen will depend on the chemical substance being detected. For example, if a hydrogen-containing substance, e.g., ammonia or ethanol, is being detected, the material must be capable of insertion of hydrogen atoms. The most preferred materials for hydrogen detection are amorphous $WO_3$ and $IrO_2$. The preferred material for ammonia detection is $HfS_2$.

Insertion element 16 is sandwiched between electrically conductive elements 12 and 14; a dielectric 5 element 18 separates insertion element 16 from electrically conductive element 14. Ohmic electrical contacts 20 and 22 connect elements 12 and 14 to conventional external a.c. circuitry 13 for measuring changes in the capacitance of sensor 10 caused by changes in the bulk electrical characteristics of insertion element 16.

Electrically conductive element 12 is preferably a catalytic metal which is capable of dissociating the chemical substance being detected into species that can insert into insertion element 16. For example, if the chemical substance is a hydrogen-containing molecule, e.g., water or ethanol, element 12 dissociates the molecule into species that include hydrogen atoms, which then diffuse through element 12 and insert into insertion element 16. The change in free energy associated with the transfer from element 12 to insertion element 16 is preferably negative to provide a thermodynamic diving force for the transfer.

The choice of catalytic metal will depend on the particular chemical substance being detected. Examples of suitable metals are Pt, Pd, Ir, Ru, Os, Fe, Ag, Au, Cu, and Ni, used alone or alloyed with each other. The metals can also be alloyed with non catalytic metals or insulators to increase the active surface area of the catalyst and to prevent surface poisoning. The catalyst can be provided in the form of halides, carbonyls, halocarbonyls, and oxides, with a noncatalystic porous contact layer, e.g. gold. Preferred catalytic metals for hydrogen detection include Pd, Pt, and Rh, most preferably Pd.

The thickness of element 12 preferably is between 50 and 1000 A to permit rapid diffusion of the catalytically dissociated chemical species. It can be deposited as a continuous film or as a grid. It is not necessary that a Schottky barrier exist at the interface between element 12 and insertion element 16.

Electrically conductive element 14 is preferably a single or polycrystalline semiconductor, e.g., p type Si or n-type Si. The thickness of element 14 ranges from 1000 A (for a thin film) to greater than 1 mm (for a free standing crystal).

Dielectric element 18 insulates insertion element 16 from electrically conductive element 14. Preferably, dielectric element 18 is $SiO_2$, $Si_3N_4$, or $Ta_2O_5$. The thickness of element 18 ranges from 50 to 1000 A, and is designed to be sufficient to prevent electrons from tunnelling between insertion element 16 and electrically conductive element 14. Both dielectric element 18 and electrically conductive element 14 are preferably continuous layers.

EXAMPLE 1

A Pd/$WO_3$/$SiO_2$/p-Si hydrogen sensor embodying the invention was prepared as follows.

A single crystalline p-type Si substrate with (100) orientation and a resistivity of 2.5 ohm-cm was selected. An oxide layer 520 A thick was grown on the surface of the Si substrate at 1100° C. in an atmosphere of dry $O_2$/3% HCl. Following oxidation, the oxide was removed from the back surface of the Si substrate, and an Al ohmic contact applied by thermal vacuum evaportion, followed by annealing in $N_2$ at 400° C. A 3600 Å thick film of amorphous $WO_3$ was then deposited on the oxidized surface by thermal evaporation in an atmosphere of pure $O_2$ ($O_2$ pressure=$5 \times 10^{-4}$ torr). Pd dots, 200 Å thick with diameters ranging from 0.5 to 2 mm were then deposited onto the $WO_3$ film by thermal vacuum evaporation, followed by annealing in $N_2$ at 400° C.

The following hydrogen sensors were also prepared using a method analogous to the above-described method: Pd/$WO_3$/$SiO_2$/n-Si; Pt/$WO_3$/$SiO_2$/p-Si; Pt/$WO_3$/$SiO_2$/n-Si; and Au/$WO_3$/$SiO_2$/p-Si.

EXAMPLE 2

Sensors in which insertion element 16 is $IrO_2$ were prepared as described above for the $WO_3$-based sensors except that the $IrO_2$ layer was deposited by reactive rf magnetron sputtering under and $O_2$ pressure of 2 $\mu$m from a pure iridium target.

EXAMPLE 3

A Pd-Au/$HfS_2$/ITO/Glass ammonia sensor embodying the invention was prepared as follows.

N-type $HfS_2$ single crystals were grown by iodine vapor transport as follows. Pure Hf powder was reduction annealed in flowing $H_2$ at 400-500° C. to reduce oxide surface layers and then annealed in a vacuum of $1 \times 10^{-6}$ torr at 450° C. for 3 hours to remove hydrogen. Next, the powder was further purified by subliming at 115° C. in vacuo and collecting the condensate on a cold finger containing dry ice and acetone.

Stoichiometric quantities of the purified Hf powder and S were placed in a quartz reaction tube (22 mm$\times$25 cm) and a quantity of iodine (5 mg/ml of tube volume) added as a transport agent. The tube was evacuated to $<1 \times 10^{-3}$ torr, sealed, and placed in a multizone furnace with the growth zone 50° C. cooler than the reactant zone. The temperature of both zones was then increased in approximately 50° C. intervals until transport to the growth zone was evident.

Next, the temperature of the growth zone was increased approximately 50° C. higher than the reactant zone to back-transport all material to the reactant zone and the temperature of the growth zone quickly reduced to c.a. 10° C. higher than the reactant zone. The temperature of the growth zone was then reduced at a rate of 2° C./hr until it was 50° C. lower than the reactant zone. These conditions were maintained for about 80 hours, in which time crystal growth occurred.

The Pd Au catalyst layer was evaporated as a series of dots onto the surface of the $HfS_2$ crystals. An ohmic contact was applied to the back surface of the crystals by applying an In/Ga eutectic. The structures were then mounted onto an ITO/glass substrate.

$HfS_2$ sensors in which the catalyst layer was Au and Pt-Au were prepared in analogous fashion.

Field Effect Transistor

Figure 2:
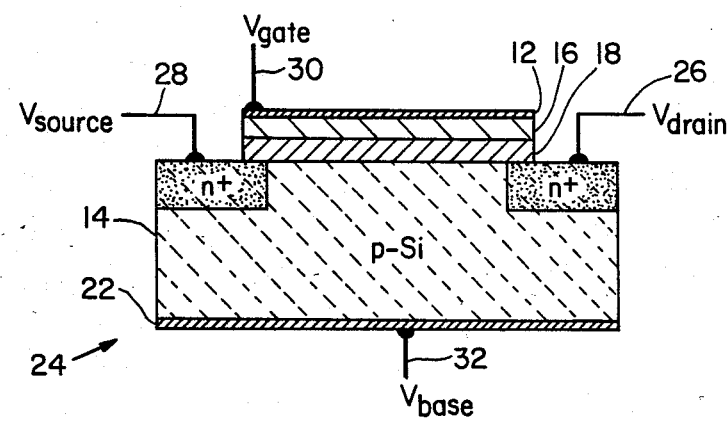

Sensor 10 is preferably incorporated as part of a field effect transistor 24, shown in FIG. 2. Transistor 24 features insertion element 16 sandwiched between electrically conductive element 12 and dielectric element 18. Dielectric element 18 contacts electrically conductive element 14, shown here as a p-type semiconductor, i.e., p-Si. Element 14 also has 2 n-type portions in electrical contact with dielectric element 18 and separated from each other by a p-type region of element 14.

A drain electrode 26 contacts one of the n-type portions, while a source electrode 28 contacts the other n-type portion. A gate electrode 30 contacts electrically conductive element 12 and is used to apply an electrical potential from a conventional external source (not shown) between gate electrode 30 and source electrode 28; this applied potential controls the conductance between drain electrode 26 and source electrode 28. A base electrode 32, connected to element 14 through ohmic contact 22, completes the circuit.

Operation

Sensor 10 can be used to detect any chemical substance which is itself capable of insertion into insertion element 16, or is capable of dissociating in the presence of a catalyst to form insertable species. Preferably, sensor 10 is used to detect hydrogen or hydrogen-containing chemical substances, e.g., water or ethanol. Sensor 10 can be operated at temperatures ranging from room temperature to 400° C. Preferred operating temperatures range from room temperature to 150° C.

Figure 3:
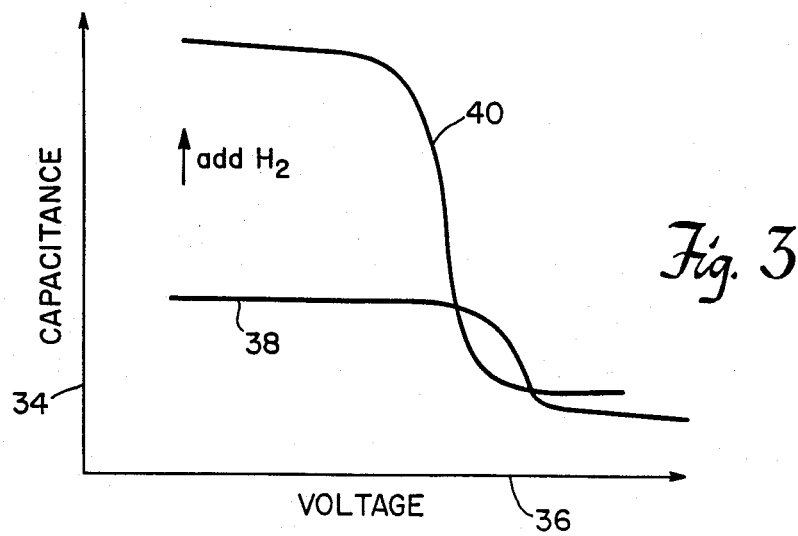
FIG. 3 is a graph showing the capacitance-voltage response of a sensor embodying the invention.

FIG. 3 shows a graph of the capacitance-voltage response of sensor 10; capacitance is plotted on a vertical axis 34, while voltage is plotted on a horizontal axis 36. Before exposure to hydrogen, sensor 10 exhibits an S-shaped capacitance-voltage curve 38, typical of conventional parallel plate metal-insulator-semiconductor capacitors. Upon exposure to hydrogen, electrically conductive element 12 catalytically dissociates the hydrogen molecules into hydrogen atoms, which diffuse through element 12 and insert into insertion element 16. Once inserted, the hydrogen atoms further dissociate to form electrons and charge-compensating hydrogen ions. These electrons and ions transforms insertion element 16 from an insulator to an electrical conductor. In addition, water molecules present in the ambient atmosphere are physisorbed and transported into the bulk of element 16 without a corresponding electron transfer.

Because insertion element 16 is now electrically conductive, the ability of insertion element 16 and dielectric element 18 to screen electrically conductive elements 12 and 14 from each other decreases. The net result of this decrease is to shift S-shaped capacitance-voltage curve 38 upwardly along vertical capacitance axis 36 to S-shaped curve 40. The physisorbed species also contribute to the capacitance change by changing the dielectric constant of element 16. Thus, the shift in capacitance represents contributions from both hydrogen and physisorbed water molecules.

Exposure to hydrogen also causes curve 40 to be shifted horizontally along x-axis 36 relative to curve 38, changing the location of the transition region. This shift is related to the change in flat band voltage of sensor 10, which is caused by electron transfer from the inserted hydrogen atoms. However, because physisorbed species do not transfer electrons, they do not contribute to this horizontal shift. Therefore, the concentrations of hydrogen and water can be measured, and their relative contributions separated from each other, by monitoring the capacitance of sensor 10 in response to an a.c. voltage applied between electrically conductive elements 12 and 14 and then separating out the contribution from the electron-transfer species by measuring the change in the flat band voltage.

To regenerate sensor 10 after hydrogen exposure, sensor 10 is exposed to air or an oxygen-enriched atmosphere. The oxygen molecules at the surface of element 12 provide a driving force for removing the hydrogen ions and electrons by promoting water formation at the surface of element 12.

When sensor 10 is incorporated as part of field effect transistor 24, the changes in the capacitance of sensor 10 upon hydrogen exposure are reflected in changes in the threshold voltage ($V_T$) of transistor 24. $V_T$ is the voltage applied between gate electrode 30 and source electrode 28 required to initiate current flow between source electrode 28 and gain electrode 26. Changes in $V_T$ are related to the concentration of hydrogen. Transistor 24 is regenerated by exposing it to air or an oxygen-enriched atmosphere to promote water formation.

The sensors of the invention can be used, e.g., as smoke detectors, humidity sensors, gas leak detectors, and alcohol analyzers for detecting alcohol in breath. Preferably, pattern recognition is used to distinguish between individual chemical substances present in the sample being analyzed. For example, a breath sample being analyzed for ethanol will also contain water. Ethanol produces a different response from water when detected by sensor 10. Thus, by comparing the sample response to the response when pure ethanol is present, it is possible to determine whether the sample contains ethanol in addition to water.

Other embodiments are within the following claims.

Dielectric element 18 can be eliminated from sensor 10 so that insertion element 16 directly contacts electrically conductive element 14; an example of such a sensor has the structure Au/WO$_3$/p-Si. In these embodiments, exposing the sensor to hydrogen causes a d.c. current to flow through the sensor as insertion element 16 becomes electrically conductive; the current is proportional to the concentration of hydrogen ions and electrons inserted in insertion element 16, and thus the hydrogen concentration. If a Schottky barrier forms between insertion element 16 and electrically conductive element 12 upon hydrogen exposure, the sensor becomes a rectifying diode. By measuring the capacitance of the diode under reverse bias, the hydrogen concentration can be determined.

Sensors in which dielectric element 18 has been eliminated can also be incorporated into field effect transistors.

Electrically conductive element 14 can also be a metal, e.g., Al or Au, or an electrically conductive ceramic, e.g., indium tin oxide (ITO). The following sensors, in which element 14 is a metal, have been prepared: Pt/WO Pd/WO$_3$/Ta$_2$O$_5$/Au; Pd/WO$_3$/Ta$_2$O$_5$/Au; Au-Pd/WO$_3$/SiO$_2$/ITO; Au-Ni/WO$_3$/SiO$_2$/ITO; Au-Cu/WO$_3$/SiO$_2$/ITO; Au-Pt/WO$_3$/SiO$_2$/ITO; Au-Ru/WO$_3$/ITO; and Au/WO$_3$/Ta$_2$O$_5$/Au. Analogous sensors in which insertion element 16 is IrO$_2$ were also prepared. In these embodiments, exposing the sensor to hydrogen changes the capacitance of the sensor, which can be measured by passing an a.c. current between electrically conductive elements 12 and 14. The sensor capacitance ($C_S$) is given by the following equation: $1/C_S = 1/C_I + 1/C_{DE}$, where $C_I$ is the capacitance of insertion element 16 and $C_{DE}$ is the capacitance of dielectric element 18. Hydrogen exposure changes $C_I$, while $C_{DE}$ remains constant.

Dielectric element 18 can also be eliminated from sensors in which electrically conductive element 14 is a metal or electrically conductive ceramic; an example of such a sensor has the structure Au/WO$_3$/ITO. In these embodiments, exposing the sensor to hydrogen causes the capacitance of the sensor to change as insertion element 16 becomes electrically conductive; the capacitance is not, however, a function of the applied voltage. Changes in the capacitance can be related to the concentration of hydrogen.

The electrical resistance of a sensor in which electrically conductive element 14 is a metal and dielectric element 18 is eliminated can also be monitored and related to hydrogen concentration.

The catalytic metal can be incorporated into the pores of insertion element 16. It can also be present with alternating or graded layers of an inert metal to increase the longevity of sensor 10.

When electrically conductive element 14 is a metal or electrically conductive ceramic, the sensor cannot be incorporated into a solid state field effect transistor. The sensor can, however, be incorporated into hybrid circuits, i.e., circuits having both semiconductor and non-semiconductor components.

The sensor can also be regenerated by simply removing the substance being detected, e.g., hydrogen gas, instead of exposing the sensor to air or an oxygen-enriched atmosphere.

Insertion of atoms or molecules into the bulk of element 16 can cause the bulk electrical conductivity of element 16 to decrease; the decrease is related to the concentration of inserted species.

The lattice constant of element 16 can be modified by reacting element 16 with any of the following materials during the fabrication of the sensor: Lewis bases, e.g., amines; organic sulfides, e.g., carbon disulfide; alkali metals, e.g., potassium; or transition metals, e.g., iron. Modifying the lattice constant modulates the selectivity of the sensor.

What is claimed is:

1. A sensor for detecting a chemical substance comprising
    an insertion element comprising a compound selected from the group consisting of IRO$_2$ and HfS$_2$ having a structure which enables insertion of said chemical substance with a resulting change in the bulk electrical characteristics of said insertion element; and
    detecting means for measuring the change in capacitance of said sensor as a manifestation of said change in said bulk electrical characteristics of said insertion element to detect the presence of said chemical substance.

2. A sensor for detecting a chemical substance comprising
    an insertion element comprising a compound selected from the group consisting of IRO$_2$ and HfS$_2$ having a structure which enables insertion of said chemical substance with a resulting change in the bulk electrical characteristics of said insertion element; and
    detecting means comprising first and second electrically conductive elements that sandwich said insertion element for detecting said change in said bulk electrical characteristics of said insertion element as an indication of the presence of said chemical substance,
    wherein at least one of said electrically conductive elements comprises a semiconductor or electrically conductive ceramic.

3. A sensor for detecting a chemical substance comprising
    an insertion element comprising a compound selected from the group consisting of IRO$_2$ and HfS$_2$ having a structure which enables insertion of said chemical substance with a resulting change in the bulk electrical characteristics of said insertion element; and
detecting means for measuring the change in said bulk electrical characteristics as an indication of the presence of said chemical substance.

4. The sensor of claims 1 or 3 wherein said detecting means comprises first and second electrically conductive elements that sandwich said insertion element.

5. The sensor of claim 4 wherein said first electrically conductive element comprises a catalytic element which serves to dissociate said chemical substance into species that can insert into the bulk of said insertion element, and said second electrically conductive element comprises a metal, semiconductor, or electrically conductive ceramic.

6. The sensor of claim 5 wherein said catalytic element is Pt, Pd, Cu, Ru, Ni, Au, or a combination thereof.

7. The sensor of claim 5 wherein said semiconductor is p-Si or n-Si.

8. The sensor of claim 5 wherein said second electrically conductive element comprises a semiconductor and said sensor is incorporated as part of a field effect transistor.

9. The sensor of claims 1, 2, or 3 further comprising a dielectric element in electrical contact with said insertion element.

10. The sensor of claim 9 wherein said dielectric element comprises $SiO_2$ or $Ta_2O_5$.

11. The sensor of claims 1, 2, or 3 wherein said chemical substance comprises hydrogen.

12. The sensor of claims 1, 2, or 3 wherein said chemical substance comprises ammonia.

13. The sensor of claim 2 wherein one of said electrically conductive elements comprises a catalytic element which serves to dissociate said chemical substance into species that can insert into the bulk of said insertion element.

14. The sensor of claim 13 wherein said catalytic element is Pt, Pd, Cu, Ru, Ni, Au, or a combination thereof.

15. The sensor of claim 2 wherein said semiconductor is p-Si or n-Si.

16. The sensor of claim 2 wherein said second electrically conductive element comprises a semiconductor and said sensor is incorporated as part of a field effect transistor.

17. A method for detecting a chemical substance comprising the steps of
providing a sensor comprising an insertion element comprising a compound selected from the group consisting of $IrO_2$ and $HfS_2$;
contacting said sensor with said chemical substance under conditions sufficient to permit effective insertion, whereupon said chemical substance inserts into the bulk of said insertion element and causes the bulk electrical characteristics of said insertion element to change; and
detecting said change in said bulk electrical characteristics of said insertion element as an indication of the presence of said chemical substance.

18. The method of claim 17 wherein said sensor is operated at a temperature below 150° C.

19. The method of claim 17 wherein said sensor is operated at room temperature.

20. The method of claim 17 wherein said change in said bulk electrical characteristics is detected by means of first and second electrically conductive elements that sandwich said insertion element.

21. The method of claim 20 wherein said first electrically conductive element comprises a catalytic element which serves to dissociate said chemical substance into species that can insert into said bulk of said insertion element, and said second electrically conductive element comprises a metal, semiconductor, or electrically conductive ceramic.

22. The method of claim 21 wherein said sensor further comprises a dielectric element in electrical contact with said insertion element, said dielectric element and said insertion element being disposed between said first and second electrically conductive elements.

23. The method of claim 17 wherein said sensor further comprises a dielectric element in electrical contact with said insertion element.

24. The method of claim 17 wherein said chemical substance comprises hydrogen.

25. The method of claim 17 wherein said chemical substance comprises ammonia.

* * * * *

UNITED STATES PATENT AND TRADEMARK OFFICE
CERTIFICATE OF CORRECTION

PATENT NO. : 4,892,834

DATED : January 9, 1990

INVENTOR(S) : R. David Rauh

It is certified that error appears in the above-identified patent and that said Letters Patent is hereby corrected as shown below:

Column 8, line 39, "IRO$_2$" should read --IrO$_2$--.

Column 8, line 51, "IRO$_2$" should read --IrO$_2$--.

Column 8, line 67, "IRO$_2$" should read --IrO$_2$--.

Signed and Sealed this

Twenty-third Day of April, 1991

Attest:

HARRY F. MANBECK, JR.

*Attesting Officer*  *Commissioner of Patents and Trademarks*

UNITED STATES PATENT AND TRADEMARK OFFICE
CERTIFICATE OF CORRECTION

PATENT NO. : 4,892,834

DATED : January 9, 1990

INVENTOR(S) : R. David Rauh

It is certified that error appears in the above-identified patent and that said Letters Patent is hereby corrected as shown below:

Column 1, line 14, "semiconductor based" should read --semiconductor-based--.

Line 30, "metal oxide" should read --metal-oxide--.

Column 2, line 7, "p type or n type" should read --p-type or n-type--.

Column 3, line 59 "M" should read --$M_xO_y$,--.

Column 4, line 12, delete "5".

Line 29, "diving" should read --driving--.

Line 49, "p type" should read --p-type.

Column 5, line 54, "Pd Au" should read --Pd-Au--.

UNITED STATES PATENT AND TRADEMARK OFFICE
CERTIFICATE OF CORRECTION

PATENT NO. : 4,892,834

DATED : January 9, 1990

INVENTOR(S) : R. David Rauh

It is certified that error appears in the above-identified patent and that said Letters Patent is hereby corrected as shown below:

Column 6, line 36, "transforms" should read --transform--.

Column 7, line 47, "indium tin" should read --indium-tin--.

Column 8, line 39, "IRO$_2$" should read --IrO$_2$--.

Line 51, "IRO$_2$" should read --IrO$_2$--.

Line 67, "IRO$_2$" should read --IrO$_2$--.

Signed and Sealed this

Fourteenth Day of July, 1992

Attest:

DOUGLAS B. COMER

*Attesting Officer*   *Acting Commissioner of Patents and Trademarks*